(12) United States Patent
Heismann et al.

(10) Patent No.: US 7,522,708 B2
(45) Date of Patent: *Apr. 21, 2009

(54) FOCUS/DETECTOR SYSTEM OF AN X-RAY APPARATUS FOR GENERATING PHASE CONTRAST RECORDINGS

(75) Inventors: Björn Heismann, Erlangen (DE);
Eckhard Hempel, Fürth (DE); Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 79 days.

This patent is subject to a terminal disclaimer.

(21) Appl. No.: 11/700,152

(22) Filed: Jan. 31, 2007

(65) Prior Publication Data
US 2007/0183581 A1    Aug. 9, 2007

(30) Foreign Application Priority Data
Feb. 1, 2006    (DE)    ........................ 10 2006 004 976
Apr. 12, 2006    (DE)    ........................ 10 2006 017 290

(51) Int. Cl.
*G21K 1/00* (2006.01)
(52) U.S. Cl. ........................................ 378/145; 378/19
(58) Field of Classification Search ................ 378/4–21, 378/70, 71, 84–87, 145
See application file for complete search history.

(56) References Cited

U.S. PATENT DOCUMENTS

| | | | |
|---|---|---|---|
| 4,782,229 A | | 11/1988 | Ernst |
| 5,812,629 A | | 9/1998 | Clauser |
| 2007/0183562 A1 | * | 8/2007 | Popescu et al. ................ 378/19 |
| 2007/0183563 A1 | * | 8/2007 | Baumann et al. ............... 378/19 |

(Continued)

FOREIGN PATENT DOCUMENTS

EP    1 447 046 A1    8/2004

(Continued)

OTHER PUBLICATIONS

Weitkamp et al., "X-ray phase imaging with a grating interferometer", Optics Express 2005, vol. 12, No. 16, pp. 6296-6304.

(Continued)

*Primary Examiner*—Courtney Thomas
(74) *Attorney, Agent, or Firm*—Harness, Dickey & Pierce, P.L.C.

(57) ABSTRACT

A focus/detector system of an X-ray apparatus is disclosed for generating projective or tomographic phase contrast recordings. In at least one embodiment, the system includes a beam source, including a focus and a focus-side source grating, arranged in the beam path to generate a field of ray-wise coherent X-rays; and a grating/detector arrangement having a phase grating with grating lines arranged parallel to the source grating for generating an interference pattern and a detector having a multiplicity of detector elements arranged flat for measuring the radiation intensity behind the phase grating. Further, the detector elements are formed by a multiplicity of elongate detection strips, which are aligned parallel to the grating lines of the phase grating. Furthermore, at least one embodiment also relates to the use of this focus/detector system in an X-ray system for generating projective recordings or in C-arc equipment or a CT system, and/or to a method for generating projective and tomographic X-ray recordings of a subject.

25 Claims, 6 Drawing Sheets

U.S. PATENT DOCUMENTS

| | | | |
|---|---|---|---|
| 2007/0183580 A1* | 8/2007 | Popescu et al. | 378/145 |
| 2007/0183582 A1* | 8/2007 | Baumann et al. | 378/145 |
| 2007/0183583 A1* | 8/2007 | Baumann et al. | 378/145 |
| 2007/0183584 A1* | 8/2007 | Baumann et al. | 378/145 |

FOREIGN PATENT DOCUMENTS

| | | |
|---|---|---|
| EP | 1 731 099 A1 | 12/2006 |
| JP | 01 106 273 A | 4/1989 |

OTHER PUBLICATIONS

D. Vaughan (ed.), "X-Ray Data Booklet", Lawrence Berkeley Laboratory, Berkley, 1986, pp. 2-28, 2-29.

U. Bonse and M. Hart, "An X-ray Interferometer", Appl. Phys. Lett., 1965, vol. 6, No. 8, pp. 155-156.

Ingal and Beliaevskaya, "X-ray plane-wave topography observation of the phase contrast from a non-crystalline object", J. Phys. D: Appl. Phys. 28, 1995, pp. 2314-2317.

R. Fitzgerald, "Phase-Sensitive X-Ray Interferometer", Physics Today, 53, 2000, pp. 23-26.

Chapman et al., "Diffraction enhanced x-ray imaging", Phys. Med. Biol. 42, 1997, pp. 2015-2025.

Wilkins et a., "Phase-contrast imaging using polychromatic hard X-rays", Nature 384, 1996, pp. 335-338.

V. Lehmann, The Physics of Macropore Formation In low Doped n-Type Silicon, J. Electrochemical Soc. 140 (10), 1993, pp. 2836-2843.

Bergmann, Schäfer, "Lehrbuch der Experimentalphysik", vol. 1, Mechanik, Akustik, Wärme, De Gruyter, Berlin, 1970, pp. 542-554.

Shack et al., J. Opt. Soc. Am. 61, 1971, p. 656.

Platt et al., "History and Principles of Shack-Hartmann Wavefront Sensing", Journal of Refractive Surgery, vol. 17, 2001, pp. 573-577.

F. Roddier, "Variations on a Hartmann theme", Opt. Eng. 29, 1990, pp. 1239-1242.

Primot et al., "Deconvolution from wave-front sensing: a new technique for compensating turbulence-degraded images", J. Opt. Soc. Am. 7(9), 1990, pp. 1598-1608.

J. C. Wyant, "White Light Extended Source Shearing Interferometer", Appl. Opt. 13, 1974, pp. 200-202.

C. L. Koliopoulos, "Radial grating lateral shear heterodyne interferometer", Appl. Opt. 19, 1980, pp. 1523-1528.

J. Primot, L. Songo, "Achromatic three-wave (or more) lateral shearing interferometer", J. Opt. Soc. Am. A, 12(12), 1995, pp. 2679-2685.

J. Primot, "Theoretical description of Shack-Hartmann wave-front sensor", Optics Communications, 222, 2003, pp. 81-92.

V. Ronchi, "Forty Years of History of a Grating Interferometer", Appl. Opt., 3(4), 1964, pp. 437-451.

Schroer et al., "Hard x-ray nanoprobe based on refractive x-ray lenses", Appl. Phys. Lett. 87, 124103, 2005.

M. Bavdaz, N. Gurker, "Coded Imaging X-ray Microprobe", X-Ray Spectrometry, 22, 1993, pp. 65-70.

Momose et al. "Tomographic image reconstruction using X-ray phase information". SPIE, vol. 2708, pp. 674-684.

Barty et al., "Time-gated medical imaging with ultrafast laser plasma x-rays", SPIE, vol. 2523, pp. 286-298.

C. J. Kotre, I. P. Birch, "Phase contrast enhancement of x-ray mammography: a design study", Phys. Med. Biol., 44, 1999, pp. 2853-2866.

Arfelli et al, "Low-dose phase contrast x-ray medical imaging", Phys. Med. Biol. 43, 1998, pp. 2845-2852.

Herrlin et al., "Contrast-Enhanced Radiography by Differential Absorption Using a Laser-Produced X-Ray Source", Investigative Radiology 32, 1997, pp. 306-310.

Grätz et al., "Time-Gated Imaging in Radiology: Theoretical and Experimental Studies", IEEE J. of selected Topics in Quantum Electronics, 2(4), 1996, pp. 1041-1048.

Murnane et al., "Ultrafast X-ray Pulses from Laser-Produced Plasmas", Science, vol. 251, 1991, pp. 531-536.

Krol et al., "Laser-based microfocused x-ray source for mammography: Feasibility study", Med. Phys. 24(5), 1997, pp. 725-732.

Piestrup et al., "A design of mammography units using a quasiminichromatic x-ray source", Review of Scientific Instruments, 72(4), 2001, pp. 2159-2170.

C. G. Schroer, B. Lengler, "Focusing Hard X Rays to Nanometer Dimensions by Adiabatically Focusing Lenses", Phys. Rev. Lett. 94, 054802, 2005.

Weitkamp et al.; X-ray phase imaging with a grating interferometer, Aug. 8, 2005, vol. 13, No. 16, Optics Express.

Pfeiffer et al.; Phase retrieval and differential phase-contrast imaging with low-brilliance X-ray sources. In: Nature Physics, 2006, vol. 2, S. 258-261.

Senoussaoui et al: Thin-film solar cells with periodic grating coupler. In: Thin Solid Films, 2004, vol. 451-452, S. 397-401.

German Office Action (dated Jul. 23, 2007).

* cited by examiner

FOCUS/DETECTOR SYSTEM OF AN X-RAY APPARATUS FOR GENERATING PHASE CONTRAST RECORDINGS

PRIORITY STATEMENT

The present application hereby claims priority under 35 U.S.C. §119 on German patent application numbers DE 10 2006 004 976.4 filed Feb. 1, 2006, and DE 10 2006 017 290.6 filed Apr. 12, 2006, the entire contents of each of which is hereby incorporated herein by reference.

FIELD

Embodiments of the invention generally relate to a focus/detector system of an X-ray apparatus for generating projective or tomographic phase contrast recordings. For example, they may relate to one including a beam source having a focus, a detector arrangement for detecting the X-radiation and a set of X-ray optical gratings, for determining the phase shift when the X-radiation passes through a subject.

BACKGROUND

In computer tomography, tomographic recordings of a subject, in particular a patient, are generally made with the aid of absorption measurements of X-rays which pass through the subject, a radiation source generally being moved circularly or spirally around the subject and a detector on the opposite side from the radiation source, usually a multiline detector with a multiplicity of detector elements, measuring the absorption of the radiation when it passes through the subject. For tomographic image compilation, tomographic section images or volume data are reconstructed from the measured absorption data of all measured geometrical rays. Absorption differences in objects can be represented very well by these computer tomographic recordings, but regions with similar chemical composition, which naturally also have a similar absorptivity, can be represented only with insufficient detail.

It is furthermore known that the effect of the phase shift when a ray passes through a subject is substantially stronger than the absorption effect of the matter through which the radiation has passed. Such phase shifts are measured in a known way by using two interferometric gratings. With respect to these interferometric measurement methods, reference is made for example to "X-ray phase imaging with a grating interferometer, T. Weitkamp et al., $8^{th}$ Aug. 2005/Vol. 12, No. 16/OPTICS EXPRESS".

In this method, coherent X-radiation passes through a subject, the X-radiation having passed through is guided through a grating pair and the radiation intensity is measured immediately after the second grating. The first grating generates an interference pattern, which forms an image of a moire pattern with the aid of the second grating on the detector lying behind. If the second grating is displaced slightly, then this likewise causes a displacement of the moire pattern i.e. a change of the local intensity in the detector lying behind, which can be determined relative to the displacement of the second grating.

If the intensity change is plotted for each detector element of this grating, i.e. for each ray, as a function of the displacement distance of the second grating, then the phase shift of the respective ray can be determined. A problem, making it unsuitable for carrying out computer tomography of sizeable objects, is that this method requires a very small radiation source since coherent radiation is needed for forming the interference pattern.

The method presented in the document cited above requires either a radiation source with an extremely small focus, so that there is a sufficient degree of spatial coherence in the radiation used. When using such a small focus, however, then a sufficient dose power for examining a sizeable object is in turn not available. It is nevertheless also possible to use monochromatically coherent radiation, for example synchrotron radiation as the radiation source, but this makes the CT system very expensive to construct so that widespread application is not possible.

This problem can be circumvented by arranging a first absorption grating inside the focus/detector combination in the beam path, immediately after the focus. The alignment of the grating lines is in this case parallel to the grating lines of the interference grating which follows after the subject.

The slits of the first grating generate a field of individually coherent rays with a particular energy, which is sufficient for generating the interference pattern known per se with the aid of the phase grating arranged behind the object in the beam direction.

In this way, it is possible to use radiation sources which have extents that correspond to normal X-ray tubes in CT systems or transmitted-light X-ray systems so that, for example, even well-differentiated soft tissue tomographs can now be made in the field of general medical diagnosis.

A problem with this type of focus/detector combination is that a plurality of measurements need to be carried out respectively with a slightly displaced analysis grating for each ray, so that it is possible to determine the phase shift of the X-radiation on the respective ray path through the subject.

SUMMARY

In at least one embodiment of the invention, a focus/detector system is provided which makes it possible at least to reduce the number of measurements required, or even to have to carry out just one measurement process on each ray in order to be able to generate projective or tomographic phase contrast recordings of a subject.

In at least one embodiment, the Inventors have discovered that instead of the previously used analysis grating, it is possible to use detector elements which comprise a multiplicity of detection strips that subdivide the individual detector element in the direction of the grating lines of an upstream phase grating, so that individual detection of strips interconnected groupwise and the individual groups are read out with respect to the dose arriving on them. Depending on the number of groups which are formed and depending on the period with which the detection strips are arranged, i.e. depending on the fineness of the individual detection strips, it is therefore now possible to resolve an individual X-ray so that either the number of measurements with which a particular X-ray is sampled can be greatly reduced or, with a correspondingly high division of the detection strips, the average phase of the respectively considered X-ray can be determined directly with a single measurement of the detection strips interconnected groupwise.

Another advantage of this focus/detector system according to at least one embodiment of the invention is that the full amount of the used dose to which the subject is exposed, in particular a patient, is now in fact used for the measurement and, unlike when an analysis grating is used, a part of the dose to which the patient has been exposed is not superfluously absorbed in the analysis grating.

According to the basic concept of at least one embodiment of the invention, the measurement of the phase shift of the X-radiation of a ray passing through a subject is thus measured in that the phase grating known per se is arranged on the detector side and, owing to the phase shift of the X-radiation when it passes through the subject, generates an interference pattern in which the phase shift is imaged. In contrast to the known variant according to which an analysis grating is subsequently placed in order to determine the phase shift by measuring the intensity change on a considered detector element or in the corresponding considered X-ray together with a minimal displacement of the analysis grating, the actual detector is now placed at the position of the analysis grating and each detector element is designed with a multiplicity of detection strips which are of the order of magnitude of the period of the previously used analysis grating. In this way, it is now possible to combine these detection gratings alternately in two steps and thereby obtain in one measurement two items of dose information, corresponding to an upstream analysis grating, there being a virtual displacement of the analysis grating by one half period between the two measurements.

If the division of the detection strips, i.e. the width of the detection strips, is now reduced further, then the detection strips may be divided into groups of three or four or more per detector element, so that the groupwise readout of the dose arriving on the detection groups can be converted directly into the phase shift of the X-ray which strikes the corresponding detector element.

In this embodiment of a focus/detector system according to at least one embodiment of the invention, it should of course be pointed out that within a ray which corresponds in its spatial extent to a detector element, or corresponds to the solid angle covered on the detector element if the focus/detector element is installed in a computer tomograph and the subject is scanned in rotation, it is naturally only possible to measure an average phase shift of the X-radiation which is represented by this considered X-ray.

According to the basic concept of at least one embodiment of the invention, a focus/detector system of an X-ray apparatus for generating projective or tomographic phase contrast recordings is now provided, which comprises:
 a beam source having a focus and a focus-side source grating, which is arranged in the beam path and generates a field of ray-wise coherent X-rays,
 a grating/detector arrangement having a phase grating with grating lines arranged parallel to the source grating for generating an interference pattern and a detector having a multiplicity of detector elements arranged flat for measuring the radiation intensity behind the phase grating,
 wherein the detector elements are formed by a multiplicity of elongate detection strips, which are aligned parallel to the grating lines of the phase grating.

It is furthermore proposed that the grating/detector arrangement should be designed and arranged so that it fulfils the following geometrical conditions:

$$p_2 = k \times p_{DS}$$
$$p_0 = p_2 \times \frac{l}{d},$$
$$p_1 = 2 \times \frac{p_0 \times p_2}{p_0 + p_2}$$
$$d = \frac{l \times d^=}{l - d^=} \text{ with } d^= = \frac{1}{2} \times \left(\frac{p_1^2}{4\lambda}\right),$$

-continued
$$h_1 = \frac{\lambda}{2(n-1)},$$

where:
$p_0$=grating period of the source grating $G_0$,
$p_1$=grating period of the phase grating $G_1$,
$p_2$=large period of the detection strips $D_s$, spacing of the interference lines after the analysis grating,
$p_{DS}$=small period of the detection strips $D_s$, distance from midline to midline of neighboring detection strips,
d=distance from the phase grating $G_1$ to the analysis grating $G_2$ or to the detection strips $DS_x$, in fan beam geometry,
$d^=$=distance from the phase grating $G_1$ to the analysis grating $G_2$ or to the detection strips $DS_x$, with parallel beam geometry,
k =2, 3, 4, 5, ...,
l=distance from the source grating $G_0$ to the phase grating $G_1$,
λ=selected wavelength of the radiation,
$h_1$=bar height of the phase grating $G_1$ in the beam direction,
n=refractive index of the grating material of the phase grating.

The arrangement according to at least one embodiment of the invention can be embodied particularly favorably with the aid of detection strips which are designed as so-called directly converting detection strips. These detection strips have the property that incident X-radiation or photons generate electrical charges which are tapped and detected via a previously applied electrical potential. The electrical charge is therefore proportional to the incident number of X-ray photons.

Such detection arrangements can be produced in a known way with correspondingly high resolution from wafers with the aid of etching methods, a corresponding number of downstream electrical circuits connected to the groupwise arranged detection strips being expedient so that the radiation incident on the detection strips can then be measured groupwise. The phase shift existing, or more precisely the average phase shift existing, of the respective X-ray can be determined directly with these measurements of the radiation intensity at the arrayed spacing of the detection strips.

According to at least one embodiment of the invention, it is furthermore proposed that the n detection strips of a detector element should be connected alternately or groupwise to readout electronics via m electronics paths for reading out the radiation intensity in steps of m, where 2=m<<n.

According to preferred variants, in at least one embodiment, of the division of the detection strips, precisely two or three or four electron paths are provided. In this case, it should be borne in mind that it is necessary to displace the detector element slightly at the position of the respective X-ray when using two electronics paths for measuring the phase shift of the X-ray so that, with the aid of two measurements multiplied by the two electronics paths, a total of four measurements are available with which the phase shift can be determined. If more than two electronics paths are used, i.e. three or more, then it is possible to determine the phase shift or an additional offset of the detector and additional measurements.

The Inventors furthermore propose, in at least one embodiment, that the focus/detector system as described above should be used either in an X-ray system which generates projective recordings, i.e. phase contrast recordings in this case. On the other hand, it is also possible to use such a focus/detector system in an X-ray C-arc system for generating projective and tomographic phase contrast recordings, or as a third alternative such a focus/detector system may be used in an X-ray CT system, in which case essentially tomographic phase contrast recordings are compiled.

It should furthermore be pointed out that computation time, in at least one embodiment, for controlling and calculating the phase shift may be provided for such X-ray systems, i.e. including C-arc systems or CT systems. As a role, this calculation is performed with the aid of a corresponding program code, which carries out a corresponding method during operation. The invention also relates to a corresponding storage medium of an X-ray system or for an X-ray system, which executes such a program code in order to carry out such a method, which will be described below.

The Inventors furthermore provide a method for, in at least one embodiment, generating projective X-ray recordings of a subject, preferably a patient, with a focus/detector system as described above, wherein at least the following method steps are carried out:

the subject is irradiated by a beam of rays, each ray in space being defined with respect to direction and extent by the focus-detector element connecting line and the extent of the detector element, the average phase shift of each ray is measured in that, for this ray, the intensity of the radiation is measured with the aid of the fine structured detection strips at detection strips connected groupwise and arranged offset with respect to one another or positioned offset from one another, phase contrast recordings, the pixel values of which represent the average phase shift per ray, are compiled from the measured average phase shifts.

This method according to at least one embodiment of the invention may be developed so that the detection strips of a detector element are connected alternately to two measurement paths and, without an intermediate detector offset, at least two intensity measurements are carried out on the two groups of detection strips via the two measurement paths of a detector element, a spatial offset of the groups of detection strips. subsequently takes place at least once, and two further measurements are carried out for the same geometrical ray.

With respect to the at least twofold measurement with a spatial offset, it is possible either to carry out this spatial offset of the groups of detection strips by circuit technology, or it is possible to carry out the spatial offset of the groups of detection strips physically. For example, this may be done with the aid of piezo elements which displace a wafer, on which the detection elements of a detector element are arranged, perpendicularly to the grating lines.

In another embodiment of the invention, the Inventors furthermore propose that the detection strips of a detector element should be connected alternately to at least three measurement paths and, without an intermediate detector offset, at least three intensity measurements should be carried out on the at least three groups of detection strips via the three measurement paths of a detector element for a ray.

BRIEF DESCRIPTION OF THE DRAWINGS

The invention will be explained in more detail below with reference to example embodiments with the aid of the figures, only the features necessary for understanding the invention being represented. Here, the following references are used: 1: CT system; 2: first X-ray tube; 3: first detector; 4: second X-ray tube; 5: second detector; 6: gantry housing; 7: patient; 8: patient support; 9: system axis; 10: control and computation unit; 11: memory; A, B, C, D: measurement paths of grouped detection strips; d: distance from the phase grating $G_1$ to the analysis grating $G_2$ or to the detector strips $DS_x$ in fan beam geometry; $d^=$: distance from the phase grating $G_1$ to the analysis grating $G_2$ or to the detector strips $DS_x$ with parallel geometry; $D_1$: detector; $DS_x$: detection strip; $E_i$: $i^{th}$ detector element; $F_1$: focus; $G_0$: source grating; $G_1$: phase grating; $G_2$: analysis grating; $h_0$, $h_1$, $h_2$: height of the grating bars; $I(E_i(X_G))$: measured intensity at the detector element $E_i$ with the grating offset $x_G$; $I_{ph}$: measured intensity of the photon flux; 1: distance from the source grating $G_0$ to the phase grating $G_1$; n: refractive index of the grating material of the phase grating; P: patient; $p_o$: grating period of the source grating $G_0$; p1: grating period of the phase grating $G_1$; p2: large period of the detector strips $D_S$, spacing of the interference lines after the analysis grating; $p_{DS}$: small period of the detector strips $D_S$, distance from midline to midline of neighboring detection strips; $Prg_n$: program; S: system axis; $S_1$, $S_2$: X-rays; w: extent of the focus; $x_G$: offset of the analysis grating or of the detector strips; x,y,x: cartesian coordinates; µ: extent of a voxel; φ: phase shift; $φ_{Ex}$ phase shift at the detector element $E_x$; Φph: photon flux; $Φ_{ph}(x)$: photon flux at the position x of a detector element; λ: wavelength of the X-radiation in question; γ: X-radiation.

The figures show the following in detail.

DETAILED DESCRIPTION OF THE EXAMPLE EMBODIMENTS

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

Figure 1:
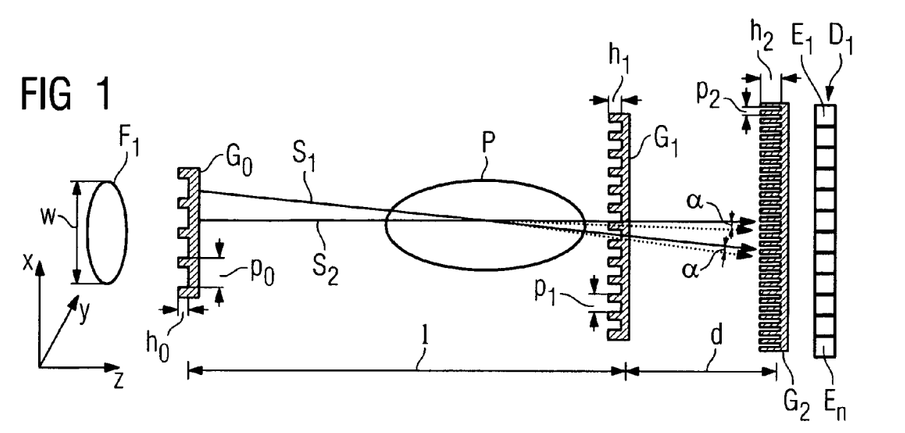
FIG. 1: longitudinal section through a focus/detector system with representation of the source grating, the phase grating and the analysis grating and their grating structure.

For better understanding of phase contrast measurement, a focus/detector system with a grating set $G_0$ to $G_2$ is shown in FIG. 1. Before the first grating $G_0$, there is a focus $F_1$ whose greatest extent is denoted by w. The first grating $G_0$ has a grating line period $p_0$ and a grating bar height $h_0$. The gratings $G_1$ and $G_2$ are correspondingly also provided with a height $h_1$ and $h_2$, respectively, and a period $p_1$ and p2, respectively. In order for the phase measurement to function, it is necessary that the distance l between the gratings $G_0$ and $G_1$ and the distance d between the gratings $G_1$ and $G_2$ should be in a particular mutual ratio. Here, $$p_0 = p_2 \times \frac{l}{d}$$

The distance of the detector $D_1$ with its detector elements $E_1$ to $E_n$ from the last grating $G_2$ is not essential. The height $h_1$ of the bars of the phase grating should be selected so that the following formula is satisfied according to the wavelengths in question, i.e. the relevant energy of the x-radiation, and in relation to the respective grating material:

$$h_1 = \frac{\lambda}{2(n-1)}$$

Here, n denotes the refractive index of the grating material and λ denotes the wavelengths of the X-rays, at which the phase shift is intended to be measured. This grating may advantageously be adjusted to an energy which corresponds to a characteristic line in the X-ray spectrum of the anode being used, and at least a sufficient photon count should be available in this energy range. With the nowadays customary tungsten anodes, for example, the $K_\alpha$ line may be used. It is nevertheless also possible to use the $K_\beta$ line lying next to it. When other anode materials are selected, different energies and therefore different dimensioning of the phase grating will correspondingly be necessary.

The height $h_2$ of the analysis grating must be sufficient in order to generate effective absorption differences between the bars through which the X-radiation passes and the substantially free positions of the grating, in order to obtain a corresponding moiré pattern on the rear side.

The line orientation of the gratings $G_0$ to $G_2$ is regularly configured so that the grating lines of all three gratings extend mutually parallel. It is furthermore advantageous, but not necessary, that the grating lines should be oriented parallel or perpendicularly to the system axis S, in which case the gratings $G_0$ to $G_2$ will usually be designed to be flat and aligned perpendicularly to the midline between the focus and detector midpoints. In principle, it is nevertheless also possible to adapt the surface of the gratings to the ray profile of the ray cone so that, at any position, the gratings are intersected by the ray connection between the focus and the respective detector element, which entails a corresponding curvature of the gratings.

Figure 2:
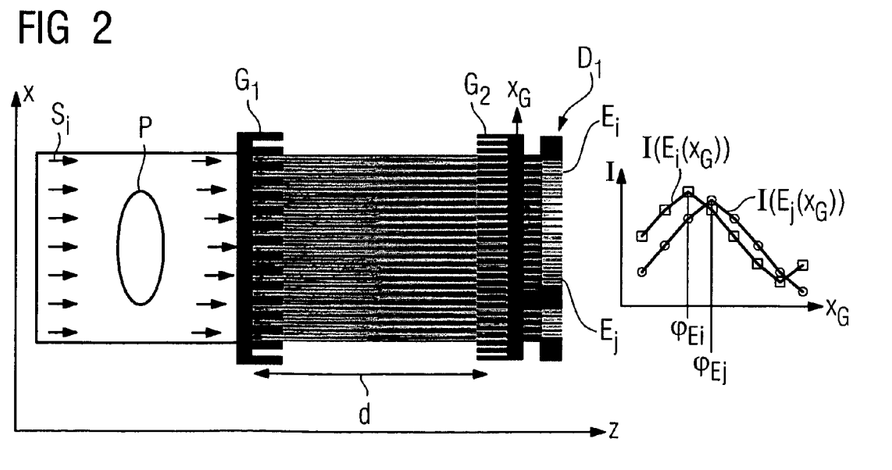
FIG. 2: longitudinal section through a focus/detector system of a CT with a phase grating, an analysis grating and a detector to represent the interference phenomenon.

FIG. 2 again shows the individually coherent radiation coming from the grating $G_0$, which passes through the patient P, phase shift phenomena taking place after it passes through the patient P. When passing through the grating $G_1$ an interference pattern is thereby generated, as represented by the gray shading, which with the aid of the grating $G_2$ leads to different radiation intensities per detector element on the downstream detector $D_1$ and its detector elements, a so-called moiré pattern being formed there. If the detector element $E_i$ for example is considered as a function of an offset $x_G$ of the analysis grating $G_2$ and the intensity $I(E_i(x_G))$ as a function of the offset $x_G$ is plotted against the intensity I, then a sinusoidal rise and fall of the intensity I at this detector element $E_i$ is obtained. If these measured radiation intensities I are plotted for each detector element $E_i$ or $E_j$ as a function of the offset $x_G$, then the function $I(E_i(x_G))$ or $I(E_j(x_G))$ can be approximated for the various detector elements, which in the end form the geometrical X-ray between the focus and the respective detector element. The phase shift p relative to one another can be determined for each detector element from the functions. The following applies:

$$\varphi = 2\pi n \frac{v}{\lambda},$$

where v corresponds to the size of a voxel or pixel in the object examined, n is its refractive index and λ represents the wavelength of the X-radiation.

For each ray in space, the phase shift per ray can therefore be determined by at least three measurements with a respectively offset analysis grating, from which either the pixel values of a projective recording can be calculated directly in the case of projective X-ray recordings, or projections whose pixel values correspond to the phase shift are compiled in the case of a CT examination, so that with the aid of reconstruction methods known per se it is possible to calculate therefrom which volume element in the subject is to be ascribed to which component of the measured phase shift. Either section images or volume data are thus calculated therefrom, which reflect the local effect of the examined object in respect of the phase shift of X-radiation. Since even minor differences exert a strong effect on the phase shift in this context, very detailed and high-contrast volume data can be obtained from materials which are relatively similar per se, in particular soft tissue.

The previously described variant of detecting phase shifts of the. X-rays which pass through a subject, with the aid of a multiple offset analysis grating and measuring the radiation intensity on a detector element behind the analysis grating, has the disadvantage that at least three measurements of each X-ray have to be carried out with a respectively displaced analysis grating. This makes the scanning of the subject relatively slow, the dosage also being increased. There is also the problem that a part of the radiation is lost from the detection owing to the analysis grating being used, since it is absorbed in the grating.

An embodiment of the invention therefore proposes to obviate such an analysis grating and instead to structure the detector elements, which are arranged following the phase grating, so that at least no dose loss occurs in the measurement, and advantageously to select a division such that the phase shift in the relevant ray can be determined by a single measurement.

Figure 3:
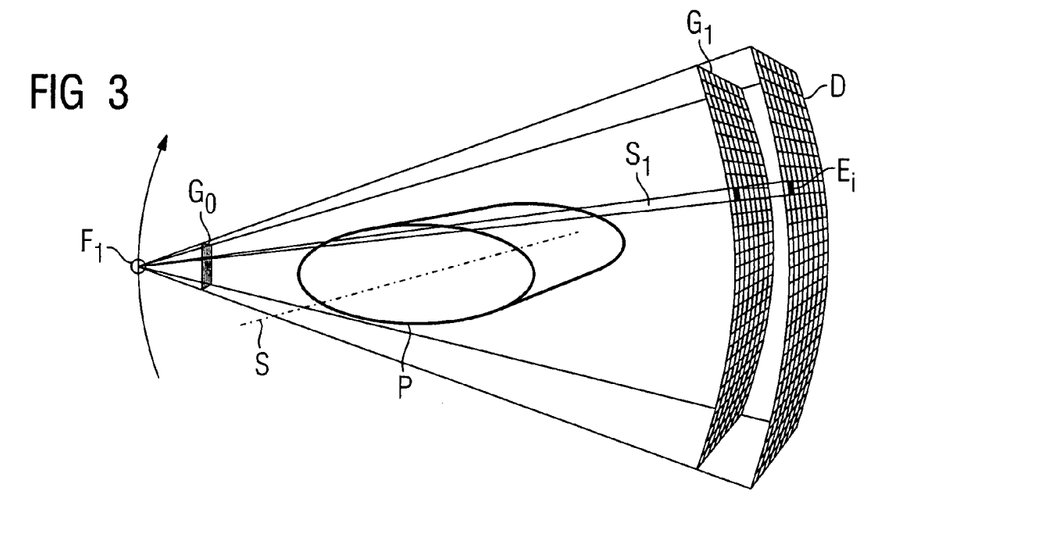
FIG. 3: schematic 3D view of a focus/detector system according to an embodiment of the invention without an analysis grating.

Such an arrangement is schematically shown in a 3D representation of a focus/detector system of a computer tomograph in FIG. 3. This shows a focus $F_1$ in whose beam path a source grating $G_0$ is arranged and on the detector side there is a phase grating $G_1$ which generates the interference phenomena described above, which are measured by the subsequent detector so that each individual detector element can measure the phase shift, or more precisely the average phase shift, of the radiation over this detector element. In the representation shown, a detector $D_1$ which is designed as a multiline detector is represented on the detector side, each line containing a multiplicity of detector elements and each detector element being preceded by a grating structure of the phase grating $G_1$.

Figure 4:
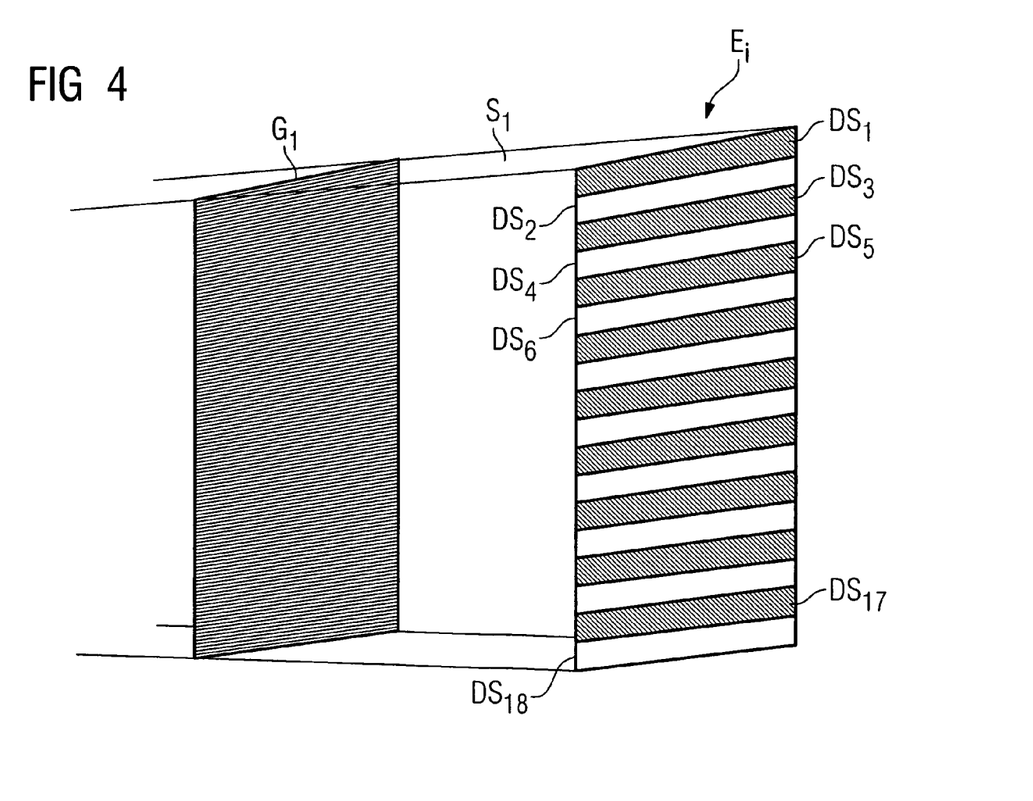
FIG. 4: three-dimensional representation of an individual detector element with an upstream phase grating.

This combination of a grating and detector element is shown on an enlarged scale in FIG. 4. Here, the detector element is represented as being structured, consisting of a multiplicity of detection strips $DS_1$ to $DS_{18}$ which are oriented in terms of their alignment parallel to the grating lines of the phase grating $G_1$. It should be pointed out that the division as shown here is merely a schematic representation, which is intended to show the basic principle of the division, the dimensions in practice being fundamentally different therefrom.

In practice, the size of such a detector element is in the range of from 100 to 1000 μm. The period $p_2$, of the order of which the extent of the detection strips must be, is generally about 2 μm so that the individual detection strips, if they are divided into two divisions, are approximately one μm.

Figure 5:
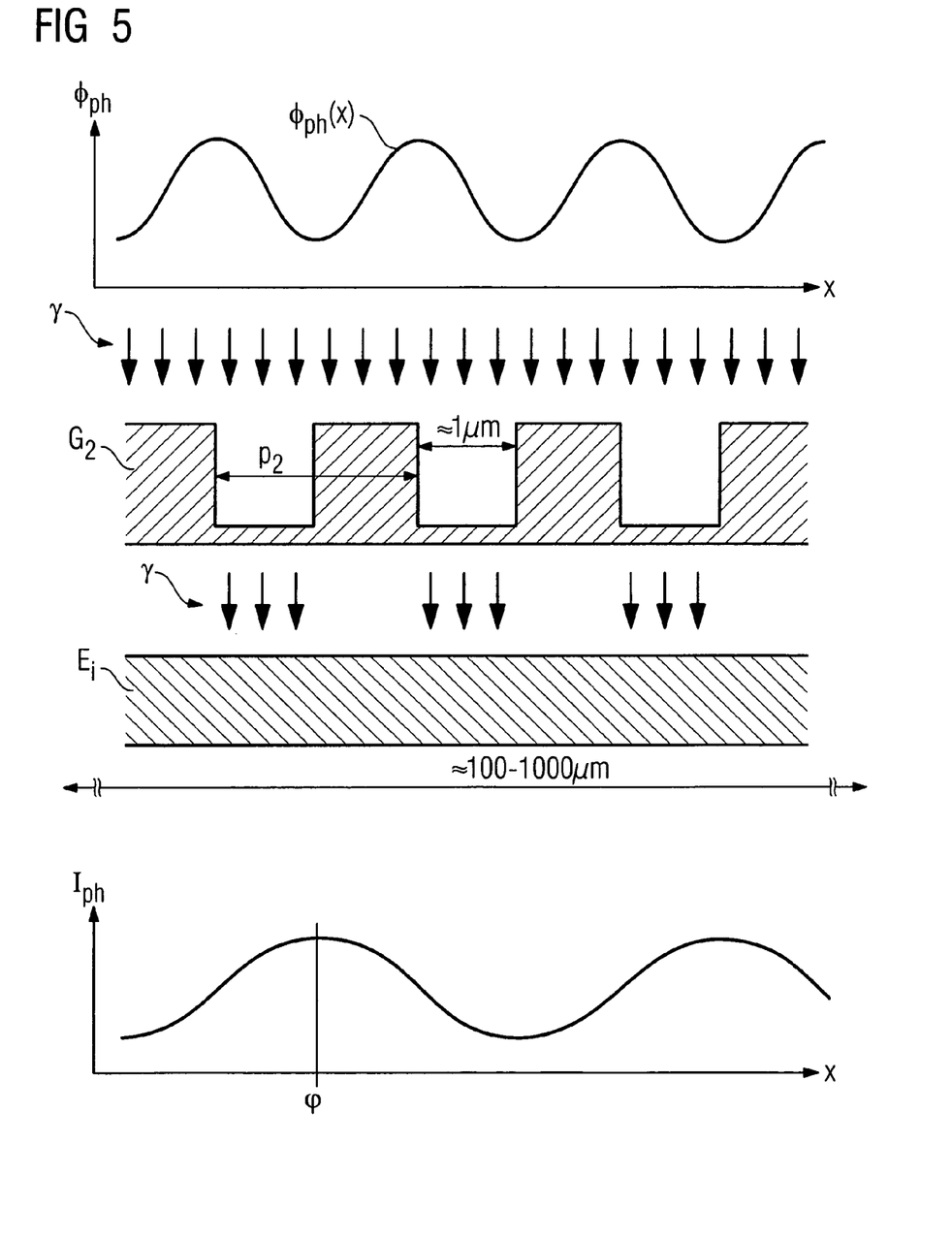
FIG. 5: schematic representation of the detection of the phase shift with an analysis grating.

FIG. 5 further illustrates the basic principle of measuring the phase shift with the aid of an analysis grating $G_2$. This representation schematically shows the flux of the X-ray photons $\Phi_{ph}$ over the x axis behind the phase grating at a spacing of one Talbot distance, the profile of the photon flux $\Phi_{ph}(x)$ being plotted against the x axis. The x axis in this case extends perpendicularly to the grating lines. The analysis grating $G_2$ is subsequently shown, which comprises a period p2 and absorbs the photons in its bars so that only at the free positions can the photons pass through downward and finally strike the detector element $E_i$ lying behind, where their intensity is measured. If the grating $G_2$ is now displaced slightly in the direction of the x axis, then a strong intensity variation of the measured radiation intensity $I_{ph}$ occurs on the detector element lying behind, which may be plotted against the length of the displacement of the grating. The phase φ can be determined for the respective detector element from the curve of the radiation intensity as a function of the offset $x_G$ of the analysis grating $G_2$.

Figure 6:
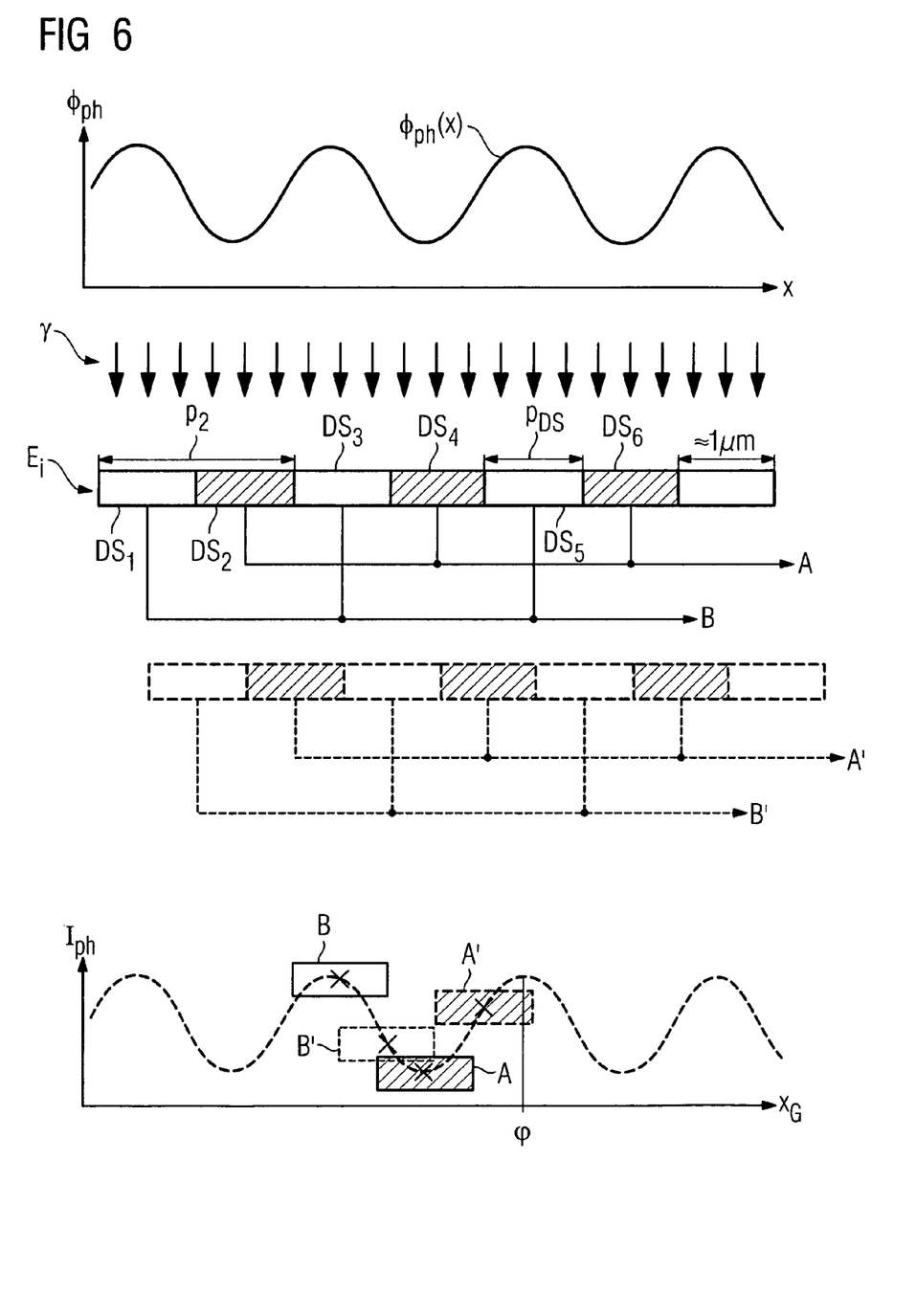
FIG. 6: schematic representation of the detection of the phase shift without an analysis grating, but with a structured detector element having detection strips in groups of two.

According to an embodiment of the invention, the analysis grating can now be replaced by imparting a grating-like structure to the detector element, in which case by combining a multiplicity of strips—corresponding to the grating lines or the free spaces in the grating—it is respectively possible to measure the intensities which pass through the grating or the intensities which correspond to an offset of one half period of a grating. Such a situation is represented in FIG. 6. The photon flux due to the interference phenomenon, which is caused by the phase grating, is here again firstly represented at the top against the x axis. This photon flux strikes the detector element with differing intensity, the detector element $E_i$ being divided into a multiplicity of detection strips $DS_1$ to $DS_6$. The detection strips are alternately combined with two different paths A and B, so that the detection strips $DS_1$, $DS_3$, $DS_5$ . . . feed the path B while the detection strips $DS_2$, $DS_4$, $DS_6$ . . . feed the path A. In this way, respectively by considering the dose measured via the path A or path B, it is possible to measure the intensity change which would result if an analysis grating—corresponding to FIG. 5—would be displaced by one half period.

If the same are measurement is carried out with a detector displaced slightly or detection strips displaced slightly by one half period of a detection strip, as indicated below by dashes, then the same measurement can be carried out with the two paths, in which case corresponding intensities are measured. If these measured intensities of the paths A and B, or with a slightly displaced detector A' and B', are plotted against the x axis, then, as in the representation shown below regarding these measured values, fitting of a sine curve can be carried out so that the phase φ of the detected X-radiation can be determined.

Figure 7:
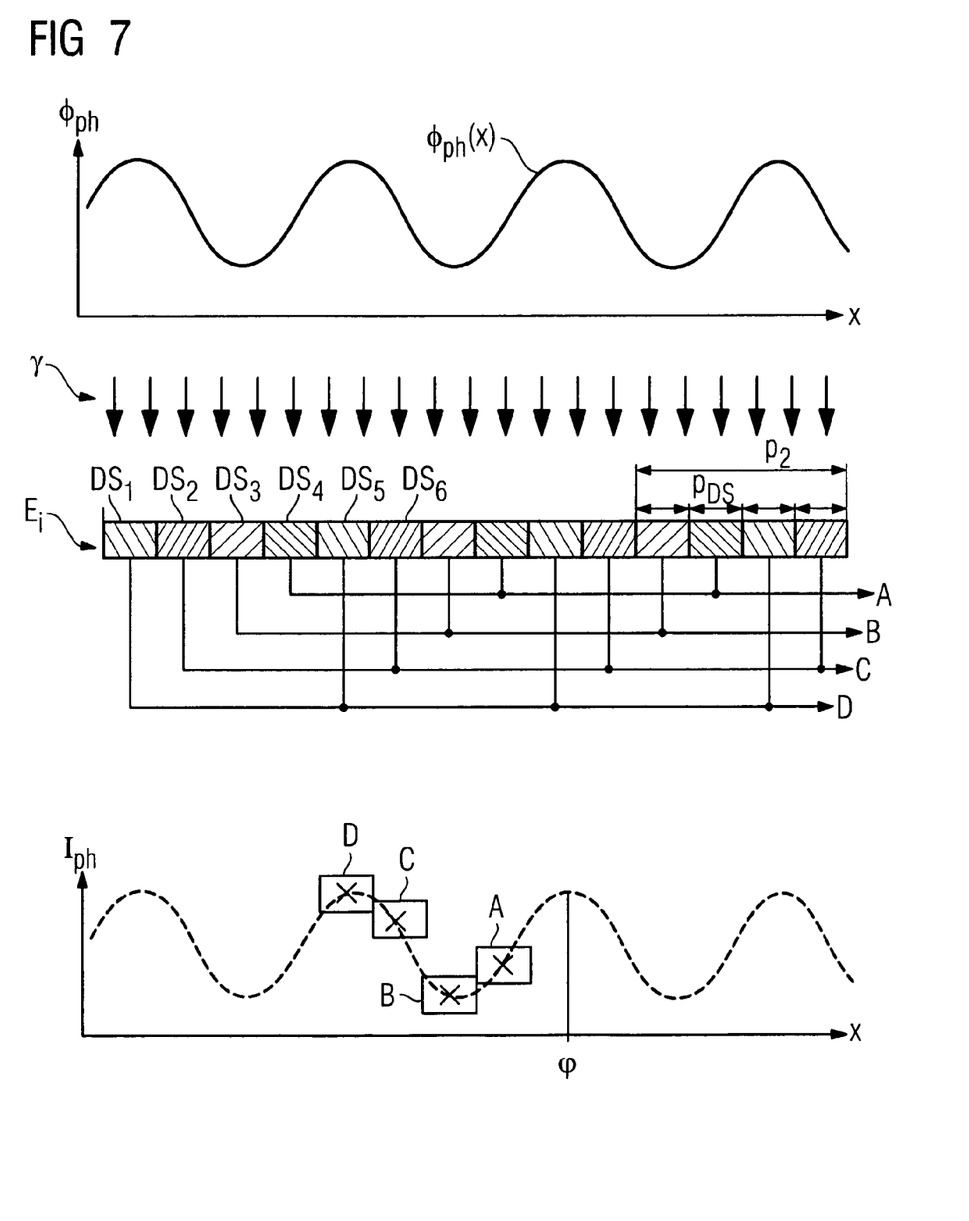
FIG. 7: schematic representation of the detection of the phase shift with a detector element having detection strips, divided into groups of four.

While it is still necessary to carry out at least two measurements with respectively offset detection strips in the alternative embodiment of FIG. 6, two measurement values being obtained here via the paths A and B for each measurement, in an improved embodiment of the detection system according to an embodiment of the invention as represented in FIG. 7, it is possible to determine the phase of the X-radiation detected by a detection element directly by a single measurement. FIG. 7 shows a detection arrangement similar to FIG. 6, although the division of the detection element into detection strips is configured so that the individual detection strips comprise merely one fourth of the period of the corresponding analysis grating. In this way, it is now possible to interconnect the detection strips so that every fourth strip is fed to the same electronics path and corresponding detection strip groups are formed.

If a measurement is now carried out with such a detector arrangement at a particular position i.e. for a particular X-ray, then the phase-corresponding intensity can respectively be read from the intensities measured via the measurement paths A, B, C and D and the phase of the X-radiation which strikes this detector element can be determined directly from these four measurements. The evaluation of these four measurement values A, B, C, D is again represented at the bottom in this figure; it should furthermore be noted here that this measurement does not correspond for instance to a phase determination of the X-radiation in the region of an individual detection strip, rather it corresponds to averaging over the entire surface of the detection element. It is particularly advantageous in this case that the entire dose used for the measurement which irradiates the subject, in particular a patient, is employed for the evaluation and no dose losses therefore occur.

The essence of an embodiment of the invention is thus that a detector element is divided into a multiplicity of detection strips, which are read out groupwise in respect of the measured X-ray intensity, the division needing to be carried out so that on the one hand it matches the period $p_2$ of a corresponding analysis grating, but at the same time it comprises at least two and preferably at least three detection strips per period so that each of the groups of detection strips is represented once per period. This type of division thus makes it possible to fit two, three, four, five or more detection strips within one period and sequence this division repeatedly in a direction perpendicular to the alignment of the detection strips, so that the number of measurement groups corresponds to the number of detection strips per period $p_2$.

Figure 8:
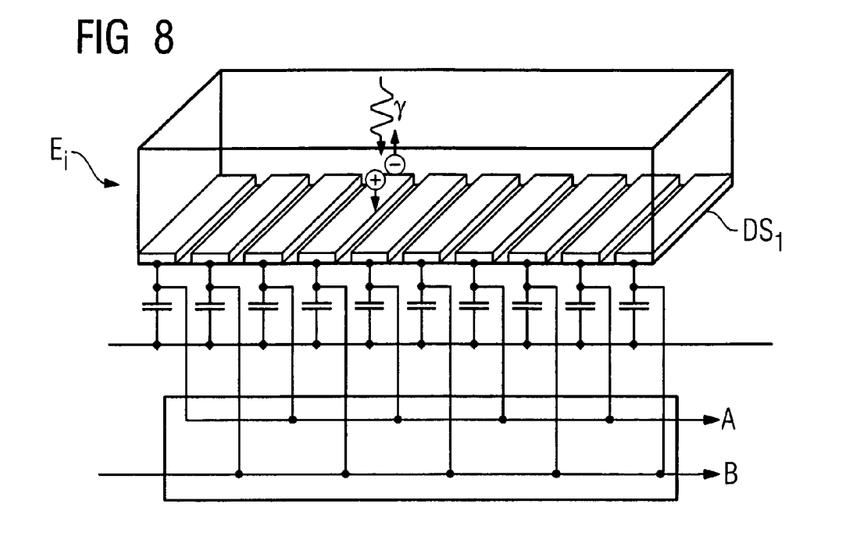
FIG. 8: 3D representation of a detector element with detection strips divided into two groups.

Such an example embodiment of a detection element is again shown in FIG. 8, the detection strips here being connected to the channels A and B in groups of two.

Figure 9:
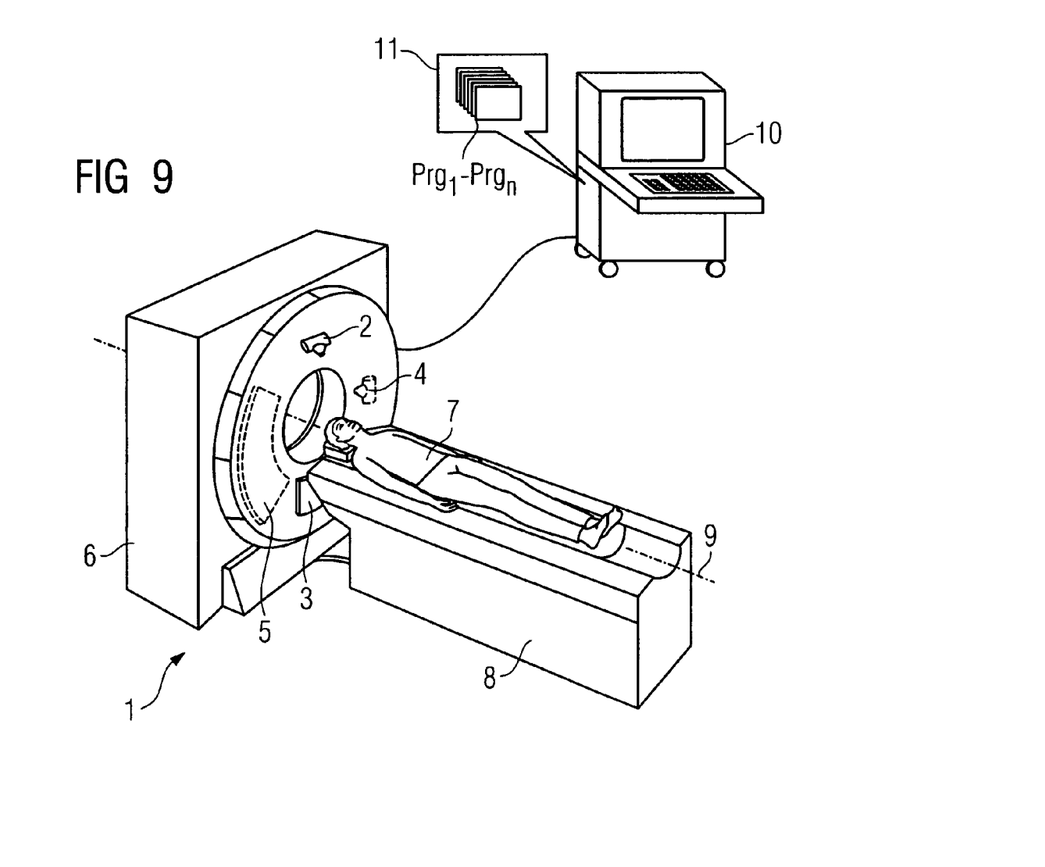
FIG. 9: X-ray CT system in 3D view with a focus/detector system according to an embodiment of the invention.

FIG. 9 represents a complete computer CT system for carrying out the method according to an embodiment of the invention. It shows the CT system 1 which comprises a first focus/detector system with an X-ray tube 2 and a detector 3 lying opposite, which is arranged on a gantry (not represented in detail) in a gantry housing 6. A grating system according to FIGS. 1 to 3 is arranged in the beam path of the first focus/detector system 2, 3 so that the patient 7, who lies on a patient support 8 displaceable along the system axis 9, can be displaced into the beam path of the first focus/detector system and scanned there. The CT system is controlled by a computation and control unit 10 in which programs $Prg_1$ to $Prg_n$ are stored in a memory 11, which carry out the method according to the invention as described above and reconstruct corresponding tomographic images from the measured ray-dependent phase shifts.

Optionally, instead of the single focus/detector system, a second focus/detector system may be arranged in the gantry housing. This is indicated in FIG. 9 by the X-ray tube 4 shown in dashes and the detector 5 represented in dashes.

Moreover, it should also be pointed out that the focus/detector systems as presented are not only capable of measuring phase shifts of the X-radiation, rather they are furthermore suitable for conventional measurement of the radiation absorption and reconstruction of corresponding absorption recordings. Optionally, combined absorption and phase contrast recordings may even be generated.

It should furthermore be pointed out that in a practical embodiment, the gaps between the grating lines in the source gratings used may be filled with a highly absorbent material to improve the contrast. For example, gold may be used for this. In principle, the source gratings should be configured so that they achieve a contrast factor of at least $e^{-1}$.

It is to be understood that the features of the invention as mentioned above may be used not only in the combination respectively indicated, but also in other combinations or in isolation, without departing from the scope of the present invention.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A focus/detector system of an X-ray apparatus for generating at least one of projective and tomographic phase contrast recordings, comprising:
    a beam source, including a focus and a focus-side source grating, arranged in the beam path to generate a field of ray-wise coherent X-rays; and
    a grating/detector arrangement including a phase grating with grating lines arranged parallel to the source grating for generating an interference pattern and a detector including a multiplicity of detector elements arranged in a plane for measuring the radiation intensity behind the phase grating, wherein the detector elements are formed by a multiplicity of elongate detection strips aligned parallel to the grating lines of the phase grating.

2. The focus/detector system as claimed in claim 1, wherein the grating/detector arrangement is designed and arranged so that it satisfies the following geometrical conditions:

$$p_2 = k \times p_{DS}$$

$$p_0 = p_2 \times \frac{l}{d},$$

$$p_1 = 2 \times \frac{p_0 \times p_2}{p_0 + p_2}$$

$$d = \frac{l \times d^\equiv}{l - d^\equiv} \text{ with } d^\equiv = \frac{1}{2} \times \left(\frac{p_1^2}{4\lambda}\right),$$

$$h_1 = \frac{\lambda}{2(n-1)},$$

where:
$p_0$=grating period of the source grating $G_0$,
$p_1$=grating period of the phase grating $G_1$,
$p_2$=large period of the detection strips $D_s$, spacing of the interference lines after the analysis grating,
$p_{DS}$=small period of the detection strips $D_s$, distance from midline to midline of neighboring detection strips,
d=distance from the phase grating $G_1$ to the analysis grating $G_2$ or to the detection strips $DS_x$ in fan beam geometry,
$d^\equiv$=distance from the phase grating $G_1$ to the analysis grating $G_2$ or to the detection strips $DS_x$ with parallel beam geometry,
k=2,3,4,5, ... ,
l=distance from the source grating $G_0$ to the phase grating $G_1$,
$\lambda$=selected wavelength of the radiation,
$h_1$=bar height of the phase grating $G_1$ in the beam direction,
n=refractive index of the grating material of the phase grating.

3. The focus/detector system as claimed in claim 1, wherein the detection strips are designed as directly converting detection strips.

4. The focus/detector system as claimed in claim 1, wherein the n detection strips of at least one detector element are connected at least one of alternately and groupwise to readout electronics via m electronics paths for reading out the radiation intensity in steps of m, where 2=m<<n.

5. The focus/detector system as claimed in claim 4, wherein precisely two electronics paths are provided.

6. The focus/detector system as claimed in claim 4, wherein at least one of precisely three electronics paths and precisely four electronics paths are provided.

7. An X-ray system for generating projective phase contrast recordings comprising at least one focus/detector system as claimed in claim 1.

8. An X-ray C-arc system for generating projective and tomographic phase contrast recordings comprising at least one focus/detector system as claimed in claim 1, arranged on a C-arc rotatable about a subject.

9. An X-ray CT system for generating tomographic phase contrast recordings comprising at least one focus/detector system as claimed in claim 1, arranged on a gantry rotatable about a subject.

10. The X-ray system as claimed in claim 7, further comprising a computation unit to control the offset of the detection strips and to calculate the phase shift from a plurality of intensity measurements of the same ray with differently offset detection strips.

11. The focus/detector system as claimed in claim 2, wherein the detection strips are designed as directly converting detection strips.

12. The focus/detector system as claimed in claim 2, wherein the n detection strips of at least one detector element are connected at least one of alternately and groupwise to readout electronics via m electronics paths for reading out the radiation intensity in steps of m, where $2=m<<n$.

13. An X-ray system for generating projective phase contrast recordings comprising at least one focus/detector system as claimed in claim 2.

14. An X-ray C-arc system for generating projective and tomographic phase contrast recordings comprising at least one focus/detector system as claimed in claim 2, arranged on a C-arc rotatable about a subject.

15. An X-ray CT system for generating tomographic phase contrast recordings comprising at least one focus/detector system as claimed in claim 2, arranged on a gantry rotatable about a subject.

16. The X-ray system as claimed in claim 8, further comprising a computation unit to control the offset of the detection strips and to calculate the phase shift from a plurality of intensity measurements of the same ray with differently offset detection strips.

17. The X-ray system as claimed in claim 9, further comprising a computation unit to control the offset of the detection strips and to calculate the phase shift from a plurality of intensity measurements of the same ray with differently offset detection strips.

18. A method for generating projective X-ray recordings of a subject with a focus/detector system of an X-ray apparatus, the focus/detector system including a beam source and a grating/detector arrangement including a phase grating and a detector including a multiplicity of detector elements, wherein the detector elements are formed by a multiplicity of elongate detection strips aligned parallel to grating lines of the phase grating, the method comprising:
  irradiating the subject by a beam of rays, each ray in space being defined with respect to direction and extent by the focus-detector element connecting line and the extent of the detector element;
  measuring the average phase shift of each ray wherein, for each ray, the intensity of the radiation is measured with the aid of fine structured detection strips at detection strips connected groupwise and arranged offset with respect to one another or positioned offset from one another; and
  compiling phase contrast recordings, the pixel values of which represent the average phase shift per ray, from the measured average phase shifts.

19. The method as claimed in claim 18, wherein the detection strips of a detector element are connected alternately to two measurement paths and, without an intermediate detector offset, at least two intensity measurements are carried out on the two groups of detection strips via the two measurement paths of a detector element, a spatial offset of the groups of detection strips subsequently takes place at least once, and two further measurements are carried out for the same geometrical ray.

20. The method as claimed in claim 18, wherein the spatial offset of the groups of detection strips is performed by circuit technology.

21. The method as claimed in claim 18, wherein the spatial offset of the groups of detection strips is performed physically.

22. The method as claimed in claim 18, wherein the detection strips of a detector element are connected alternately to at least three measurement paths and, without an intermediate detector offset, at least three intensity measurements are carried out on the three groups of detection strips via the three measurement paths of a detector element for a ray.

23. An X-ray system for generating projective phase contrast recordings comprising a computation and control unit including program code to carry out, when executed, the method as claimed in claim 18 during operation.

24. A storage medium at least one of for an X-ray system and of an X-ray system, the storage medium containing program code to carry out, when executed by the X-ray system, the method as claimed in claim 18 during operation of the X-ray system.

25. A computer readable medium including program segments for, when executed on a computer device of an X-ray system, causing the X-ray system to implement the method of claim 18.

* * * * *